United States Patent [19]
Lippel, Jr. et al.

[11] 3,984,802
[45] Oct. 5, 1976

[54] FEATURE RECOGNITION SYSTEM

[75] Inventors: Lewis G. Lippel, Jr., Warminster; Paul F. Reimel, Warrington, both of Pa.

[73] Assignee: The United States of America as represented by the Secretary of the Navy, Washington, D.C.

[22] Filed: June 27, 1966

[21] Appl. No.: 561,685

[52] U.S. Cl................ 340/5 H; 324/77 K; 340/5 R; 340/146.3 Q; 343/5 SA
[51] Int. Cl.$^2$...... G01V 1/00; G01R 23/16
[58] Field of Search............... 331/94.5 R; 340/5 R, 340/5 H, 146.3 Q, 148; 179/1 SB, 1 SP; 343/5 SA; 324/77 K

[56] References Cited
UNITED STATES PATENTS 3,054,999  9/1962  Forbath et al. .............. 343/5 MM
3,155,451  11/1964  Dunster et al. ............... 346/1

*Primary Examiner*—Maynard R. Wilbur
*Assistant Examiner*—S. C. Buczinski
*Attorney, Agent, or Firm*—G. J. Rubens; Henry Hansen

EXEMPLARY CLAIM

9. A feature recognition system for identifying an unknown signal source, comprising:
   first means for receiving a signal from the unknown signal source and producing a hologram thereof;
   second means for receiving the hologram and for correlating it with a signal reference of known sources; and
   third means associated with said second means for identifying the unknown source.

10 Claims, 4 Drawing Figures

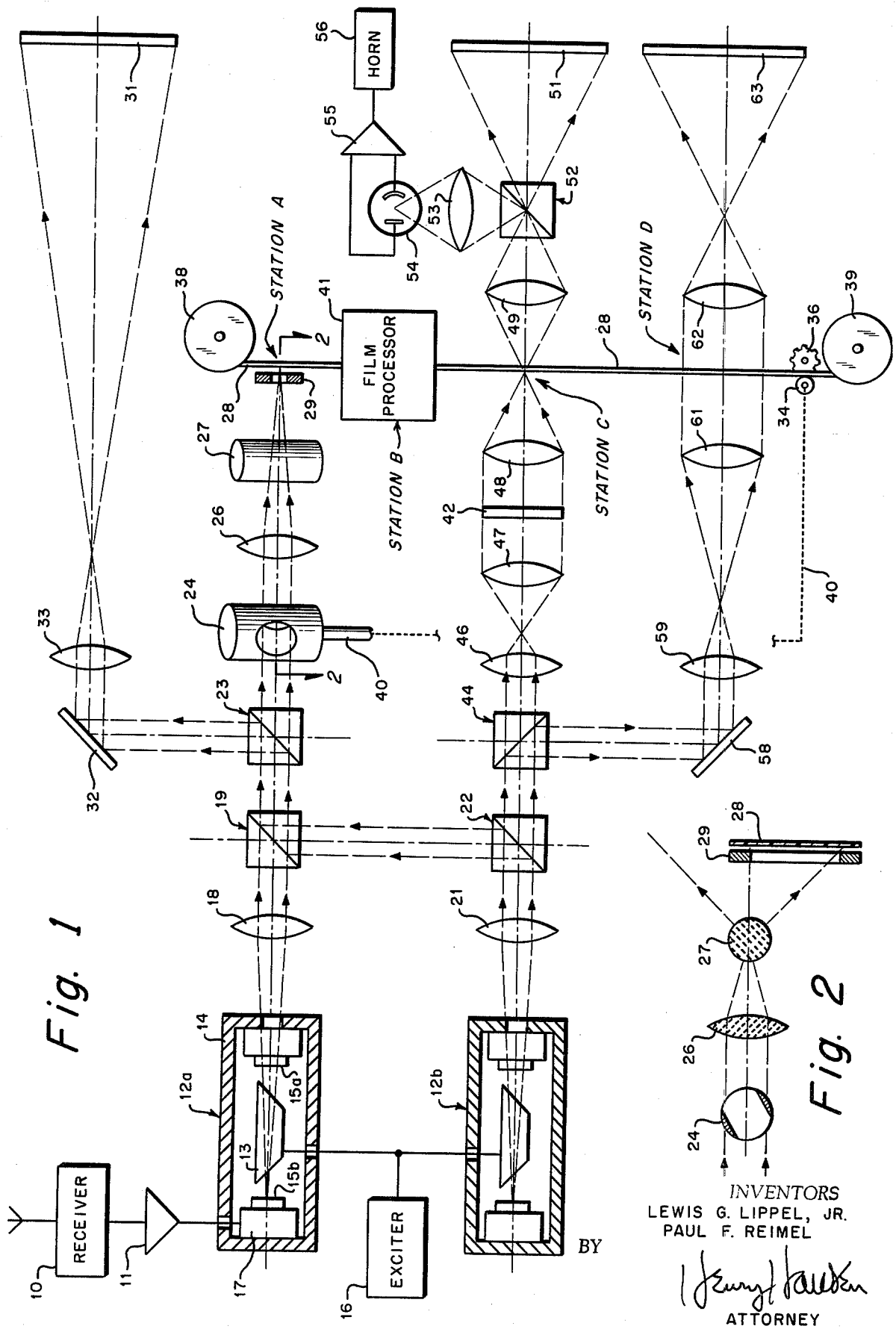

FEATURE RECOGNITION SYSTEM

The invention described herein may be manufactured and used by or for the Government of the United States of America for governmental purposes without the payment of any royalties thereon or therefor.

The present invention relates to feature recognition systems, and more particularly to a system for recognizing the acoustical signatures of underwater sound soureces and correlating the signature with known underwater sound source signatures.

It is generally known that each type or class of submarines, when submerged, generate a plurality of discrete underwater acoustical frequencies from propeller cavitation, inboard machinery, etc. The complex composite wave formed thereby is unique as a "signature" and can be used for recognition and identification. In ASW (antisubmarine warfare) it is desirable and often necessary to positively identify these signatures as opposed to those of other underwater sound sources when the submarine position has been localized and before executing appropriate action such as attack if the sound source were an enemy submarine. The most commonly known means for identifying acoustical signatures requires a frequency spectrum analysis. The acoustical signals detected by a sonobuoy are translated in an analyzer into a frequency spectrum and displayed on a recorder having a constant speed strip chart and a constant speed reciprocating and traversing pen. The line made by the pen is intensity modulated in accordance with the frequency predominance producing thereby a plurality of light and dark lines parallel to the length of the chart in coordinates of time vs. frequency. The AN/AQA-5 Sonobuoy Indicator Group, for example, produces such a display by taking 0.2 microsecond samples of the sonobuoy transmitted signal and integrating each frequency in the samples so that the line intensity produced by the pen varies with the frequency repetition rate. Noise frequencies appear as light lines because their frequency repetition rates are practically zero, while a cavitating submarine generates discrete frequencies which occur in every sample and therefore appear as dark lines because of the high frequency repetition rate.

As applied to ASW and under average noise conditions, about three inches of recordation is deemed necessary for a skilled operator to positively recognize and identify an underwater object's acoustical signature. At conventional chart speeds of about 1 inch per minute, this imposes about three minutes of delay between when an object is first encountered and when a decision for appropriate action can be made. This delay may seriously derogate the effectiveness of ASW missions, particularly in this age of fast-moving submerged submarines.

The present invention contemplates an entirely new technique of feature recognition which automatically and instantaneously recognizes and positively identifies underwater object acoustical signatures by means of optical correlation of holograms. This is accomplished with a first laser beam which is frequency modulated in accordance with a sonobuoy-detected signal and its output is superimposed with a second laser beam of constant frequency. The resulting beam is intermittently exposed on photographic film which is developed to form a hologram of an interferometric frequency spectrum. An optical cross-correlator then compares the hologram with a "master" film which contains a matrix of frequency spectra for all of the known acoustical signatures of submarine types and other underwater objects which may be encountered. If the hologram contains the same signature as one of the known signatures in the master, a spot of light will pass to a viewing screen. The vertical and horizontal position coordinates of the light spot corresponds to and indicates the type of object detected. The unique capability of lasers to instantaneously reproduce the frequency spectrum in coherent light beams has alleviated the need for complex frequency spectrum analyzers of the prior art. More importantly, the time required by the prior art systems to obtain an identifiable pattern of frequency distribution has been substantially eliminated along with the need for a skilled operator.

Accordingly, it is an object of the present invention to provide a novel feature recognition system for recognizing and identifying radiating energy sources, in which complex waves of radiated energy from an unidentified source is instantaneously translated into its frequency spectrum, and is automatically correlated with frequency spectra of known energy sources, and any correlation resulting therefrom is instantaneously indicated to an operator.

Another object is to provide novel apparatus for recognizing and identifying the radiated energy signals from a plurality of known radiated energy signals.

A still further object is to provide a feature recognition system which is particularly suitable for ASW operations in which sonobuoy-detected acoustical signatures of underwater sound sources are instantaneously recognized and identified for prompt and appropriate action thereby diminishing the chances of an ineffective or aborted mission due to a fast-maneuvering enemy submarine.

Still another object is to provide a feature recognition system which is particularly suitable for use as airborne equipment in ASW operations for recognizing and identifying submerged submarine which is relatively simple in construction and operation, which alleviates the need for highly skilled personnel for maintenance and operation, which eliminates possible errors in judgment by the human operator, and which is light weight and occupies relative little aircraft space.

Various other objects and advantages will appear from the following description of one embodiment of the invention, and the most novel features will be particularly pointed out hereinafter in connection with the appended claims.

In the drawings:

FIG. 1 is a diagrammatic representation of one embodiment of a feature recognition system of the present invention as applied to an airborne ASW equipment;

FIG. 2 is a cross sectional view through the optical axis of a portion of the embodiment of FIG. 1 taken along the line 2—2;

Figure 3:
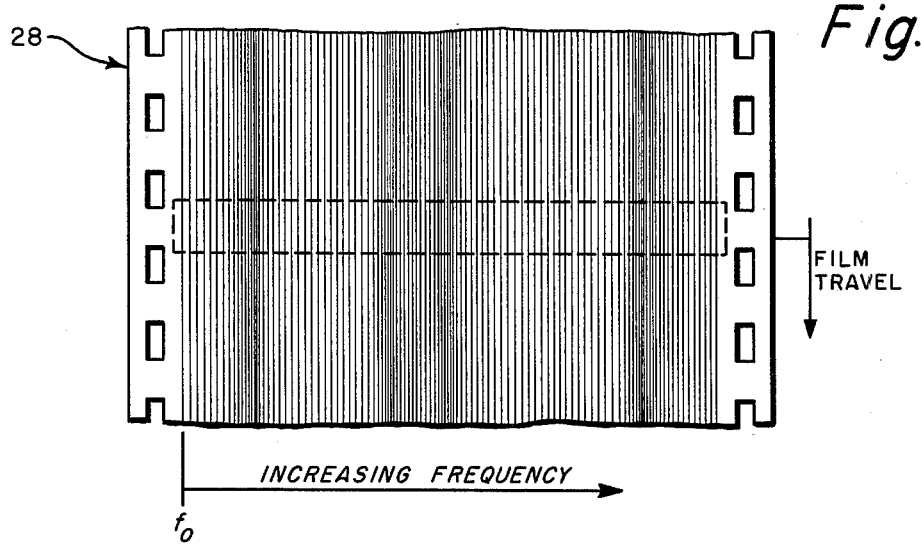
FIG. 3 represents a fragment of photographic film, produced by the embodiment of FIG. 1 and as viewed with coherent light, of a spectral frequency pattern of the acoustical signature of an imaginary type of submarine.

Referring now to the embodiment of FIG. 1, there is illustrated a radio receiver 10, such as the Navy's AN/ARR-52 Sonobuoy Receiving Set, which receives and detects FM r-f signals transmitted from a sonobuoy, not shown, on a standard transmission frequency. The sonobuoy may be any conventional type, preferably having an omnidirectional sensitivity such as the Navy's AN/SSQ-28 Sonobuoy, which is capable of detecting underwater acoustical signals propagated from submerged sources and of retransmitting these signals to an airborne receiver. The receiver 10 demodulates the signal received back into an audio frequency range representative of the complex form received by the sonobuoy from an underwater sound source. This signal is fed into a buffer or voltage amplifier 11 for producing an output control signal suitable for frequency modulating a laser 12a which may be of any conventional type capable of external modulation. In the embodiment illustrated a helium-neon (He-Ne) gas laser is contemplated having a fundamental output wavelength of 6328 angstroms of $4.82 \times 10^3$ Mc with maximum deviation of 1200 Mc, peak-to-peak, at 10 to 3000 cps external modulation. A Model 119 laser by Spectral-Physics, Inc., Mountain View, California has been found satisfactory for this purpose. A plasma tube 13 is mounted in the cavity of an Invar resonator structure 14 having one dielectric resonator mirror 15a fixed to the structure 14 and an opposing mirror 15b mounted on a fixed piezoelectric element 17. The output control signal from the amplifier 11 is applied to the element 17 causing it to expand and contract in a direction along the length of the cavity changing the cavity length between mirrors 15a and b and thereby changing the frequency of the resonant modes. Excitation of the plasma tube 13 from a high voltage power supply or exciter 16 consequently produces a modulating frequency of coherent light output through a collimating lens 18 to a beam splitter 19. The so-called beam splitter 19 may be any conventional optical device such as opposed prisms which will divide a beam coming from one direction into two beams leaving in different directions.

A constant frequency laser 12b powered by the exciter 20 is similar to the laser 12a except that it has a fixed cavity length, thereby providing a constant frequency coherent light beam which passes through a collimating lens 21 to another beam splitter 22. A portion of the constant frequency beam is reflected to the beam splitter 19 and superimposed on the portion of the modulated frequency beam conducted straight through forming thereby an interferometric beam.

An explanation of the characteristics of the interferometric coherent light formed by superposition of a constant and modulated frequency coherent light is well known to persons skilled in the art. For example, see "Model 119 Gas Laser, Operation and Maintenance Manual", Issue B, 4/1/64, *Spectra-Physics Incorporated*, Mountainview, California, and "An Introduction to Optics of Coherent and Non-coherent Electromagnetic Radiations" by George W. Stroke, Electrical Engineering Department, University of Michigan, Ann Arbor, Michigan. For purposes of this disclosure, it should be sufficient to say that the coherent light beam resulting from the superposition of the light beams of one constant frequency laser and one frequency modulated laser will produce, when exposed on photographic films, a hologram which is the Fourier analysis (spectrum) of the complex signal used to modulate the piezoelectric element 17.

The interferometric coherent light beam from the beam splitter 19 is directed to another beam splitter 23 where the straight through portion passes to a shutter 24 which intermittently passes the beam through a condensing lens 26 and a cylindrical lens 27. The beam thereby converges to a focal point on a photographic strip film 28 at station A. As shown in FIG. 2, the cylindrical lens 27 magnifies the beam in the dimension transverse to the length of the film 28 producing thereby a visual representation or hologram of the interferometric light beam in a frequency spectrum analysis. The interferometric pattern of the coherent light beam is characterized by zero frequency at the center of the beam, with frequency increasing with radial distance from the center. Since the frequency spectrum is symmetrical about the center or optical axis of the beam, it is only necessary to record the spectrum on one side of center in the magnified direction. An iris 29 is therefore provided to limit the film exposure to a very narrow transverse area of the film. As shown in FIG. 3, a portion of the length of the film 28 is superimposed with a broken line to show the outline of area exposed by the iris 29. FIG. 3 also shows a frequency spectrum or signature of an imaginary submarine as viewed on the processed film 28 with coherent light. The sound source appears on the film with the predominant frequencies appearing as dark lines parallel to the length of the film. The abscissa is in units of frequency, and the ordinate in units of time.

To permit an operator to view in real time the acoustical signature being recorded on the film 28, the beam splitter 23 reflects a portion of the interferometric coherent light beam to a separate viewing plate 31 via a mirror 32 and projecting lens 33.

The unexposed photographic film is intermittently transported by a motor 34 and sprocket 36 from a supply reel 38 past the iris 29 and the exposed and developed or processed film is stored on a take-up reel 39. To insure synchronous shutter operation with film transport, the shutter 24 is also mechanically linked by a shaft 40 to the motor 36. After the film 28 is exposed at Station A, it is passed through a film processor 41 at processing Station B where the frequency spectrum is photographically developed and fixed forming thereby a hologram. The hologram, when viewed with incoherent light such as from an incandescent source, in unintelligible; however, when viewed with coherent light, the frequency spectrum is clearly visible such as illustrated in FIG. 3. It is contemplated that the film processor be of the rapid processing type in order that the hologram produced thereby can be cross-correlated with relatively short lag time after exposure, i.e., less than 20 seconds. The process employing Kodak bimat film such as described in Kodak Pamphlet No. P-63, is satisfactory for this purpose.

Figure 4:
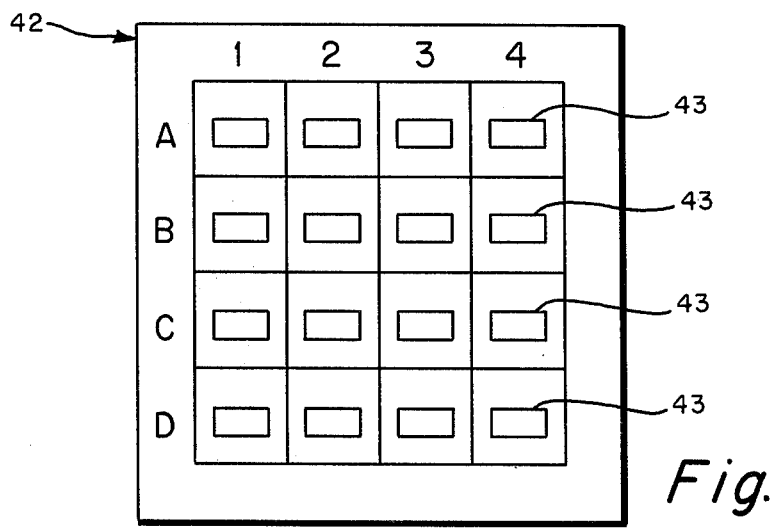
FIG. 4 represents a typical matrix of spectral frequency patterns of acoustical signatures of known types of underwater sound sources.

From the processing Station B, the film then advances to a cross-correlation Station C where the hologram is cross-correlated with a frequency spectrum signature master 42. Referring to FIG. 4, the master 42 comprises a matrix of distinct frequency spectra or acoustical signatures 43 of known underwater sound sources on transparent film and arranged in rows and columns identified numerically and alphabetically, respectively. For example, the signature in Column 2, Row B, may be the signature of a specific class of submarines, while the signature in Column 4, Row C, may represent the signature of a different specific class of submarines. The number of signatures included in the master 42 would be limited only by design and the number of known signatures pertinent to the intended use of the invention. Positive recognition and identification of the unknown acoustical signature occurs when the hologram on the film 28 arrives at Station C. The portion of the coherent light beam which passes straight through beam splitter 22 is directed to another beam splitter 44 wherein the portion thereof which passes striaght through is directed to a converging lens 46 and then a collimating lens 47. The lenses 46 and 47 form thereby collimated rays of the coherent constant frequency light beam for illuminating the entire signature master 42. The collimated light which passes through the transparent areas of all of the signatures 43 are condensed to a focal point on the film 28 by a condensing lens 48. If the unknown acoustical signature on the film 28 as viewed with coherent light is identical to one of the known acoustical signatures 43, the coherent light beam will pass through the film 28 to a projecting lens 49 and a viewing screen 51.

The surface of the screen 51 is divided by visible lines into rows and columns of equal rectangular areas each corresponding in position and identification to the rows and columns of signatures 43 of the master 42. Thus, when an unknown acoustical signature, recorded as a hologram on the film 28, corresponds to a signature 43 at a particular column and row on the master 42, a spot of light will appear at the same column and row on the screen 51. By the spot's position, the operator may then quickly identify the unknown signature.

Continuous monitoring of the viewing screen 51 is not necessary because an audible alarm system will indicate when such a spot, irrespective of its position, appears on the screen 51. That is, a beam splitter 52 having its diagonal surface positioned at the focal point of the lens 49 laterally reflects a portion of the coherent light beam through a condensing lens 53 to a photocell 54 for actuating an alarm system which includes an amplifier 55 and a horn 56.

A series of consecutive holograms of the detected acoustical signature is also viewable at Station D through which the processed film 28 passes after cross-correlation Station C. This enables the operator to visually inspect and evaluate the detected acoustical signature recorded over a time period. A laterally reflected portion of the coherent light beam from beam splitter 44 is directed to a diagonal mirror 58, through a condensing lens 59, and a collimating lens 61 for illuminating a relatively large area of the film 28 at Station D. A lens 62 projects the series of acoustical signatures contained in the illuminated area onto another viewing screen 63.

The operator is thereby presented with four distinct indicia of detected underwater sound sources. First, viewing screen 31 presents an interferometric frequency spectrum or acoustical signature of the sound source as it is received by the receiver 10 and recorded at Station A. Second, a horn 56 audibly alerts the operator of the occurrence of a cross-correlation between a known signature on the master 42 and the unknown signature on the hologram of film 28. Third, the viewing screen 51 identifies by the column and row position of a spot of light for the particular acoustical signature detected. And fourth, the viewing screen 63 displays to the operator the recorded acoustical signature over a span of time.

From the foregoing description, some of the many advantages of the feature recognition system of the present invention should now be apparent. The need for complex space and time consuming frequency spectrum analyzers has been obviated. The frequency signature of a radiating energy source is displayed instantaneously as compared to several seconds for conventional equipment. The incoming signature does not have to be processed, changed or translated. The system will give a discrete signal to an operator when a recognizable signature exists thereby removing any chance of human error in judgment. It is also capable of presenting a historical picture of the signature for comparison over a span of time.

It will be understood that various changes in the details, materials, steps and arrangements of parts, which have been herein described and illustrated in order to explain the nature of the invention, may be made by those skilled in the art within the principle and scope of the invention as expressed in the appended claims.

What is claimed is:

1. A feature recognition system for identifying the source of a radiated energy signal comprising, in combination:
    receiver means adapted to receive the radiated signal and for producing an electrical output control signal modulated according to the radiated signal;
    first laser means electrically connected to said receiver means to receive the control signal and for producing a first collimated coherent light beam at its output having a frequency which varies according to the control signal;
    second laser means for producing a second collimated coherent light beam at its output having a constant frequency;
    first optical means positioned to receive said first and second beams for superimposing one of said light beams on the other producing thereby a third collimated coherent light beam at its output with interferometric lines;
    second optical means positioned to receive and condense said third beam and adapted to receive photosensitive film for exposing the film to said third beam at the focal point;
    processor means positioned to receive the exposed film from said second optical means and develop the film forming thereby a hologram; and
    third optical means positioned to receive said second beam and adapted to receive said hologram for cross-correlating the features of a reference with said hologram, the reference having the recognizable unique features of a known radiated energy source imaged on a transparent material.

2. The combination of claim 1 further comprising:
    fourth optical means interposed between said first and second optical means for receiving said third beam means displaying a portion thereof.

3. The combination of claim 2 wherein said fourth optical means further comprises:
    reflecting means receiving said third beam and changing the direction of a portion thereof;
    lens means positioned to receive and condense said beam portion; and screen means positioned in the focal plane of said lens to receive and display said condensed beam portion.

4. The combination of claim 2 further comprising:
    fifth optical means interposed between said first and third optical means for receiving said second beam and adapted to receive the exposed film for displaying over a predetermined duration the feature recorded on the film by said second optical means.

5. The combination of claim 4 wherein said fifth optical means further comprises:
reflecting means receiving said second beam and changing the direction of a portion thereof;
first lens means positioned to receive and modify the cross-sectional area of said beam portion for illuminating a predetermined portion of the film;
second lens means positioned to receive and condense said beam portion passing through the film; and
screen means positioned in the focal plane of said second lens to receive and display said condensed beam portion.

6. The combination of claim 1 wherein said second optical means further comprises:
film transport means for intermittently transporting the film sequentially through said second optical means, said processor means, and said third and fifth optical means;
shutter means drivingly connected to said film transport means positioned to receive and intermittently pass said third beam to the unexposed film;
lens means interpositioned between said shutter means and the film condensing said third beam to a focal point on the film and magnifying said condensed beam in a direction transverse of film travel; and
iris means interpositioned between said lens means and the film for occluding all but a narrow radial cross sectional area of said condensed beam.

7. Apparatus as set forth in claim 1 wherein said third optical means comprises:
first lens means receiving and modifying the cross-sectional area of said second beam for illuminating the reference;
second lens means interpositioned between the reference and the film to receive and condense said second beam passing through the reference at a focal point on the film;
third lens means having a focal point at the film for projecting the second beam which passes through the film; and
screen means positioned at the focal plane of said second lens means for positionally displaying said projected second beam.

8. The combination of claim 7 further includes an audible indicating means comprising:
reflecting means positioned at the other focal point of said projected second beam for changing the direction of a portion of said second beam;
lens means positioned with one focal point at said reflecting means;
light responsive means positioned at the other focal point of said condenser lens means for producing an electrical signal in response to said second beam received at said other focal point; and
alarm means connected to said light sensitive means for providing an audible signal.

9. A feature recognition system for identifying an unknown signal source, comprising:
first means for receiving a signal from the unknown signal source and producing a hologram thereof;
second means for receiving the hologram and for correlating it with a signal reference of known sources; and
third means associated with said second means for identifying the unknown source.

10. An acoustical signature recognition system for identifying an underwater sound source comprising, in combination:
receiver means adapted to receive an RF signal from a sonobuoy and for producing an electrical output control signal modulated according to the acoustical signal detected by the sonobuoy;
first laser means electrically connected to said receiver means to receive the control signal and for producing a first collimated coherent light beam at its output having a frequency which varies according to the control signal;
second laser means for producing a second collimated coherent light beam at its output having a constant frequency;
first optical means positioned to receive said first and second beams fro superimposing one of said beams on the other producing thereby a third collimated coherent light beam at its output with interferometric lines indicative of the frequency spectrum of the sonobuoy-detected acoustical signal;
second optical means positioned to receive and condense a third beam and adapted to receive photosensitive film for exposing the film to said third beam at the focal point;
processor means positioned to receive the exposed film from said second optical means and develop the film forming thereby a hologram of the frequency spectrum of the sonobuoy-detected signal; and
third optical means positioned to receive said second beam and adapted to receive said hologram for cross-correlating the acoustical signatures of a reference with said hologram, the reference having a plurality of recognizable unique acoustical signatures of known underwater sound sources imaged on a transparent material.

* * * * *